(12) United States Patent
Riesinger

(10) Patent No.: US 10,595,914 B2
(45) Date of Patent: Mar. 24, 2020

(54) ROD INSERTION WITH ADJUSTABLE ROD ANGULATION

(71) Applicant: SILONY MEDICAL INTERNATIONAL AG, Frauenfeld (CH)

(72) Inventor: Ralf Riesinger, Tuttlingen-Nendingen (DE)

(73) Assignee: SILONY MEDICAL INTERNATIONAL AG, Frauenfeld (CH)

( * ) Notice: Subject to any disclaimer, the term of this patent is extended or adjusted under 35 U.S.C. 154(b) by 5 days.

(21) Appl. No.: 15/768,746

(22) PCT Filed: Sep. 15, 2017

(86) PCT No.: PCT/EP2017/073272
§ 371 (c)(1),
(2) Date: Apr. 16, 2018

(87) PCT Pub. No.: WO2018/054774
PCT Pub. Date: Mar. 29, 2018

(65) Prior Publication Data
US 2018/0303523 A1 Oct. 25, 2018

(30) Foreign Application Priority Data

Sep. 23, 2016 (DE) .................. 10 2016 011 521

(51) Int. Cl.
*A61B 17/70* (2006.01)
(52) U.S. Cl.
CPC ...... *A61B 17/7085* (2013.01); *A61B 17/7083* (2013.01); *A61B 17/7011* (2013.01); *A61B 17/7089* (2013.01)
(58) Field of Classification Search
CPC .... A61B 17/7083–7088; A61B 17/7074–7088
See application file for complete search history.

(56) References Cited

U.S. PATENT DOCUMENTS

| 7,476,240 B2 * | 1/2009 | Raymond .......... A61B 17/7002 606/279 |
| 7,588,575 B2 * | 9/2009 | Colleran ................ A61B 5/103 606/252 |

(Continued)

FOREIGN PATENT DOCUMENTS

| DE | 102013107308 A1 | 1/2015 |
| WO | 2008130548 A1 | 10/2008 |

(Continued)

OTHER PUBLICATIONS

German Office Action dated May 5, 2017, issued in the priority application DE102016011521.1.

(Continued)

*Primary Examiner* — Jacqueline T Johanas
*Assistant Examiner* — Michelle C Eckman
(74) *Attorney, Agent, or Firm* — Young Basile Hanlon & MacFarlane, P.C.

(57) ABSTRACT

The invention relates to a rod insertion device (10) for the insertion of a fixation rod (1) into a pedicle screw, comprising a receiving body (20), which has, at its distal end, a receiving recess (22) with opposite guide grooves (24), a clamping body arranged displaceably in the receiving body (20) for clamping the transverse rod in the receiving groove of the rod insertion device, wherein, in an entry area, the guide grooves of the receiving recess (22) are formed in a first direction in the receiving body (20) and, in a force-fitting area behind the entry area, are formed in a second direction different from the first direction, with the result that an inserted fixation rod is blocked in the first direction and/or in that a blocking element (30) is further provided with a detent (32), which is mounted movable between a release position and a blocking position.

12 Claims, 2 Drawing Sheets

(56) References Cited

U.S. PATENT DOCUMENTS

| | | | | |
|---|---|---|---|---|
| 7,758,584 | B2* | 7/2010 | Bankoski | A61B 17/00234 606/104 |
| 8,246,624 | B2* | 8/2012 | Forton | A61B 17/7089 606/246 |
| 8,323,286 | B2* | 12/2012 | Justis | A61B 17/708 606/86 A |
| 8,414,590 | B2* | 4/2013 | Oh | A61F 2/4611 606/86 A |
| 8,777,954 | B2* | 7/2014 | McLean | A61B 17/7032 606/86 A |
| 9,539,034 | B2* | 1/2017 | Biedermann | A61B 17/7004 |
| 9,795,422 | B2* | 10/2017 | Dauster | A61B 17/7085 |
| 9,907,582 | B1* | 3/2018 | Olea | A61B 17/7079 |
| 2005/0131419 | A1* | 6/2005 | McCord | A61B 17/7085 606/99 |
| 2005/0131420 | A1* | 6/2005 | Techiera | A61B 17/7002 606/99 |
| 2006/0036254 | A1* | 2/2006 | Lim | A61B 17/7086 606/86 R |
| 2006/0079894 | A1* | 4/2006 | Colleran | A61B 5/103 606/86 A |
| 2006/0247630 | A1* | 11/2006 | Iott | A61B 17/701 606/86 A |
| 2007/0191836 | A1* | 8/2007 | Justis | A61B 17/7002 606/279 |
| 2008/0077138 | A1* | 3/2008 | Cohen | A61B 17/708 606/86 A |
| 2008/0125788 | A1* | 5/2008 | Cohen | A61B 17/7076 606/104 |
| 2010/0249856 | A1* | 9/2010 | Iott | A61B 17/7085 606/86 A |
| 2010/0312279 | A1* | 12/2010 | Gephart | A61B 17/3421 606/264 |
| 2011/0152940 | A1* | 6/2011 | Frigg | A61B 17/7002 606/264 |
| 2011/0152942 | A1* | 6/2011 | Oh | A61B 17/7002 606/279 |
| 2011/0152952 | A1* | 6/2011 | Oh | A61B 17/7085 606/86 A |
| 2011/0184464 | A1* | 7/2011 | Fiorella | A61B 17/7089 606/264 |
| 2011/0313464 | A1* | 12/2011 | McLean | A61B 17/708 606/279 |
| 2012/0130429 | A1* | 5/2012 | Mitchell | A61B 17/7004 606/259 |
| 2012/0179214 | A1* | 7/2012 | Geist | A61B 17/7002 606/86 A |
| 2013/0012984 | A1* | 1/2013 | Wall | A61B 17/7083 606/206 |
| 2013/0150905 | A1* | 6/2013 | Karpowicz | A61B 17/7083 606/86 A |
| 2014/0039567 | A1* | 2/2014 | Hoefer | A61B 17/708 606/86 A |
| 2014/0046388 | A1* | 2/2014 | Reichen | A61B 17/7083 606/86 A |
| 2014/0074106 | A1* | 3/2014 | Shin | A61B 17/7079 606/104 |
| 2014/0088647 | A1* | 3/2014 | Baynham | A61B 17/7004 606/246 |
| 2014/0100613 | A1* | 4/2014 | Iott | A61B 17/7074 606/279 |
| 2014/0249592 | A1* | 9/2014 | Black | A61B 17/7004 606/86 A |
| 2014/0276896 | A1* | 9/2014 | Harper | A61B 17/7086 606/104 |
| 2014/0277166 | A1* | 9/2014 | Brinkman | A61B 17/7083 606/279 |
| 2014/0277197 | A1* | 9/2014 | Brown | A61B 17/7086 606/86 A |
| 2015/0051653 | A1* | 2/2015 | Cryder | A61B 17/7004 606/86 A |
| 2015/0066042 | A1* | 3/2015 | Cummins | A61B 17/7037 606/104 |
| 2015/0105832 | A1* | 4/2015 | Gleason | A61B 17/7085 606/86 A |
| 2016/0038197 | A1* | 2/2016 | Semingson | A61B 17/708 606/86 A |
| 2016/0143674 | A1* | 5/2016 | Harris | A61B 17/7085 606/279 |
| 2017/0135735 | A1* | 5/2017 | Hawkes | A61B 17/7086 |
| 2017/0340367 | A1* | 11/2017 | Beger | A61B 17/7002 |

FOREIGN PATENT DOCUMENTS

| | | |
|---|---|---|
| WO | 2011109507 A2 | 9/2011 |
| WO | 2012018792 A1 | 2/2012 |

OTHER PUBLICATIONS

PCT/EP2017/073272, International Search Report; dated Feb. 1, 2018.

Written Opinion of the International Search Authority for PCT/EP2017/0732272.

* cited by examiner

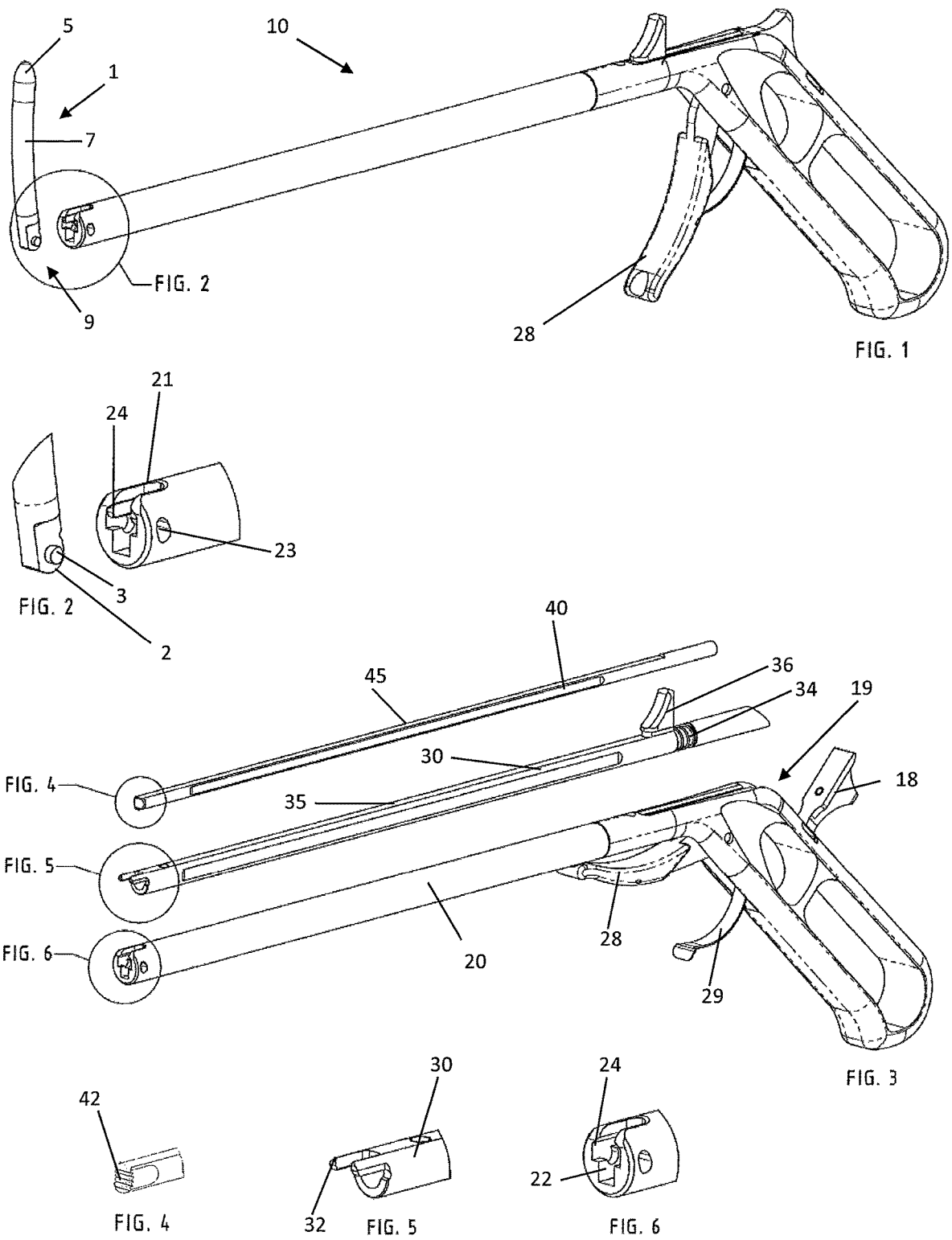

ROD INSERTION WITH ADJUSTABLE ROD ANGULATION

CROSS REFERENCE TO RELATED APPLICATIONS

This application is a national application filed under 35 USC 371 of PCT Application PCT/EP2017/073272 filed 15 Sep. 2017 and claims priority from DE 10 2016 011 521.1 filed 23 Sep. 2016 both applications incorporated by reference in their entireties for all purposes.

FIELD OF THE INVENTION

The invention relates to a rod insertion instrument with adjustable rod angulation for the insertion of a fixation rod for pedicle screws.

STATE OF THE ART

In the state of the art, rod insertion instruments are usually used which hold the fixation rod at the end in a predetermined position. Thus, the fixation rod is then pushed through two adjacent pedicle screws. In the state of the art, the fixation rods are fixed, for example, by screw mechanisms. Thus, in DE 10 2013 107 308 A1, a rod insertion instrument for the insertion of a fixation rod into the tulips of adjacent pedicle screws is described, which discloses a grip portion, a tube section adjoining it and a gripping head carried by the tube section, in which gripping head the fixation rod is receivable with its proximal end in a rotationally fixed and angularly stable manner, wherein the connection between fixation rod and gripping head is releasable by means of a manually drivable sliding body. The gripping head on the tube section is attached exclusively via a lockable joint, which enables an unconstrained pivoting movement of the tube section toward the fixation rod during the process of fixing the fixation rod to the pedicle screw. Here, the fixation rod is secured via a screw. However, such a screw implies a certain effort for securing and especially for releasing the fixation rod after the operation and forces the user to bring his hands close to the inserted fixation rod for unscrewing the fastening. An increased risk of injury to the patient can thereby also arise.

In WO 2008/130548 A1 another instrument is shown, which can hold the rod in a particular angular position. For this purpose, first of all the rod is grasped by L-shaped grippers and then pushed into the desired angular position via a push rod. However, the operating lever for the push rod can be accidentally tightened further during the operation, which alters the angular position of the rod.

BRIEF DESCRIPTION OF THE INVENTION

The object of the present invention is to provide a rod insertion instrument which, on the one hand, provides a simple and flexible adjustability of the fixation rod on the rod insertion instrument but, at the same time, enables a stable, secure but nevertheless easy-to-open fixing of the fixation rod.

A rod insertion device according to the invention for the insertion of a fixation rod into a pedicle screw comprises an in particular elongated receiving body, which has, at its distal end, a receiving recess with opposite side grooves, a clamping body arranged displaceably in the receiving body for clamping the transverse rod in the receiving recess of the rod insertion device, wherein, in an entry area, the in particular hook-shaped or curved side grooves of the receiving recess are formed in a first direction in the receiving body and, in a force-fitting area behind the entry area, are formed in a second direction different from the first direction, so that an inserted fixation rod is blocked in the first direction and/or wherein a blocking element is further provided in the receiving body, which, in particular along the entry direction of the receiving recess, is mounted movable between a release position and a blocking position and in particular is mounted displaceable in a translational manner. Both by means of the side groove with a change of direction and by means of the blocking element and, in particular, through the combination thereof, it can be ensured that the fixation rod can no longer fall out of the insertion position in the rod insertion device by accident. In particular, the side groove is at least partially formed as a through hole. The production of the side groove is thereby very simple, in particular if a second area is provided in a second direction.

In the rod insertion device, at the distal end of the blocking element, preferably provided is at least one blocking protrusion, which, in the blocking position, protrudes into the receiving groove. Such a protrusion protruding into the side groove above the bolts of the fixation rod is outstandingly suitable for holding the fixation rod in position without fixing it rotationally in an angular position at the same time. The angular position relates to the position of the fixation rod relative to the rod insertion device.

In the rod insertion device, the blocking element is mounted in particular spring-loaded in the receiving body and is pre-stressed in the blocking position. It can thereby be assured that the blocking element is also reliably seated in its blocking position without the user having to check this.

At the proximal end, the blocking element has a slide lever for the displacement. With this lever, the blocking element can be simply operated with one hand without the user having to run the risk, directly at the distal end of the rod insertion device, of touching something by accident at the operation site. This minimization of risk is extremely useful precisely while releasing the fixation rod from the rod insertion device.

At its distal end, the clamping body of the rod insertion device preferably has a tapering geometry, in particular a tip or a tooth, or is formed tooth-shaped. The tooth-shaped formation is preferably formed on an inward-curving concave surface at the distal end of the clamping body. The angular position of the fixation rod can thus be fixed very simply since the proximal end of the fixation rod is loaded with a high pressure in a small area and the fixation rod can thereby no longer rotate. In another embodiment, the clamping body is formed semi-circular at its distal end and in particular has one or more teeth, like a toothed wheel. When the proximal end of the fixation rod is then formed complementary, the angular position of the fixation rod can be fixed very simply and specially reliably.

The receiving body, the clamping body and in particular also the blocking element are preferably formed as longitudinally extending bodies, in particular as cylinder bodies with any desired external geometry (circular, elliptical, rectangular, square, hexagonal, etc.). Through this embodiment it is possible simply to arrange the different bodies in each other or around each other.

The clamping body is preferably arranged in the blocking element and the blocking element is arranged in the receiving body. A space-saving embodiment is thereby ensured. Another embodiment of the invention of the rod insertion device in such that, on the receiving body, a handle is formed in the shape of a pistol. With this ergonomic shape of the handle, in particular in the case of an angled arrangement of the fixation rod, it is easier to insert the rod. In addition, the one-handed operation of the different functions at the proximal end is thereby simple to carry out.

At the proximal end, the rod insertion device preferably has, at the end of the receiving body, a closable assembly opening. The rod insertion device is thus easier to assemble and disassemble and thus also easier to clean for re-use. In particular, the clamping body can be pressed against a clamping area of the fixation rod by means of an operating lever. The clamping body can thereby be pushed against the fixation rod with increased force, which increases the strength and security with which the fixation rod is held fast.

The clamping body and the blocking element are preferably secured via a closing in the receiving body. This increases the security against an inadvertent or accidental disassembly of the component parts of the rod insertion device. In particular, both can also be disassembled by opening the closing for cleaning purposes. Simple handling for the cleaning is thereby provided.

BRIEF DESCRIPTION OF THE FIGURES

FIG. 1 shows an isometric view of a rod insertion device according to the invention;

FIG. 2 shows an enlargement of the distal end of the rod insertion device according to the invention from FIG. 1;

FIG. 3 shows an exploded view of the rod insertion device according to the invention from FIG. 1;

FIGS. 4 to 6 show enlargements of the distal ends of the component parts of the rod insertion device according to the invention from FIG. 3;

DESCRIPTION OF THE PREFERRED EMBODIMENTS

Figure 7:
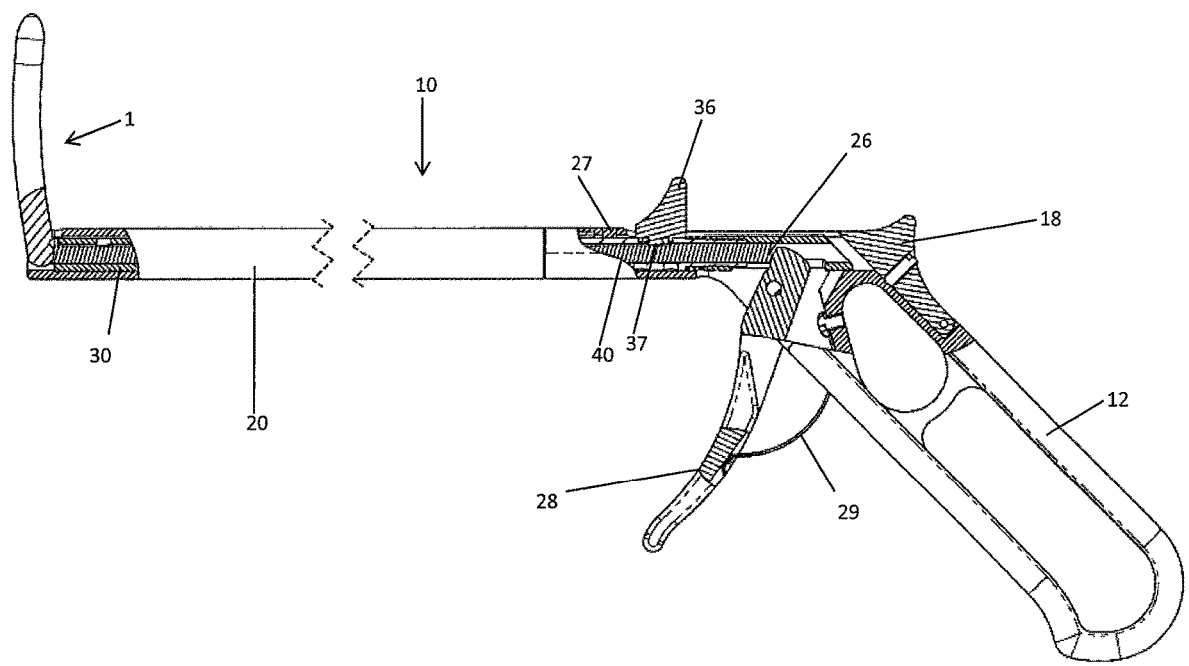
FIG. 7 shows a longitudinal section of the rod insertion device according to the invention from FIG. 1.

In the following, the terms axial, radial and circumferential as well as distal and proximal are used. Axial means a direction along the longitudinal axis of the instrument shown in FIG. 1, radial means a direction perpendicular to this longitudinal axis and circumferential means a direction around the longitudinal axis. Furthermore, the designations top, bottom, left and right are also used in relation to the instrument represented in FIG. 1. Distal refers to a side which points away from the user and proximal refers to the side directed towards the user.

The preferred embodiment of the rod insertion device 10 is represented in FIG. 1. The rod insertion device essentially consists of an elongated main body, which is formed as a receiving body 20 and has, at a distal end, a receiving apparatus 22 for a fixation rod 1 and, at the other proximal end, a handle 12 for operating and guiding the instrument.

Figure 8:
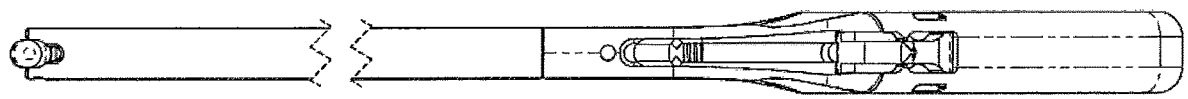
FIG. 8 shows a top view of the rod insertion device according to the invention from FIG. 1.

The fixation rod 1 can be seen in FIGS. 1, 7 and 8. There, it is formed as a slightly bent rod, which has a conical tip 5, a bent section 7 and a holding section 9. The holding section 9 is formed flattened on two opposite sides, wherein bolts 3 project on the flat sides. The holding section 9 is then held by the rod insertion device.

In the present embodiment, the rod insertion device 10 comprises the receiving body 20, a blocking element 30 arranged in the receiving body 20 and a clamping body 40 arranged in the blocking element 30 for clamping the fixation rod 1 in the rod insertion device 10. The receiving body 20, the blocking element 30 and the clamping body 40 are made elongated in the present embodiment. The rod insertion device 10 can thereby be made long enough to perform a safe operation. The handle can be made arbitrary, but in the present case it is formed as a pistol grip; it is therefore at an angle to the rest of the receiving body 20. The clamping body 40 is provided displaceable in the receiving body 20 and is operated at the handle with an operating lever 28. The operating lever can preferably be fixed in an operating position. A continuous locking device can be formed with a threaded spindle and a corresponding lock nut, for example; a stepwise locking device can be formed as a toothed rack or locking bar. However, the locking device is to be releasable at least from the operating lever and/or from the handle, with the result that the operating lever can be freely folded upwards for the assembly described later, as is shown in FIG. 3. The operating lever 28 is shown in FIG. 7. When the handle is in the user's hand, index finger and middle finger can push the operating lever at the contact point 26 against the rear part of the clamping body and press the clamping body against the fixation rod 1 with force increased by the lever arm. Then, at the distal end, the clamping body 40 thereby clamps a fixation rod 1 introduced into the receiving recess 22. The operating lever 28 is pre-stressed with a spring 29, which pushes the operating lever 28 back into the unstressed position.

The receiving recess 22 is formed at the front, distal end of the rod insertion device 10. However, the receiving recess 22 can also be provided circumferentially at the distal end, for example on the upper side. The blocking element 30 and the lateral guide grooves 24 described below must then be adapted accordingly. The receiving recess 22 has one guide groove 24 on each side for the guide bolts of the fixation rod. The guide groove 24 runs in a first direction on entry and then makes a deflection. In the embodiment shown, the guide groove 24 runs in the first area along the longitudinal axis of the receiving element and then downwards, with the result that the guide grooves 24 run in a hook shape or curved, e.g. like a bayonet catch. This change of direction of the guide grooves 24 makes it more difficult for the fixation rod to accidentally fall out of the groove when it is in its end position and is fixed by the clamping body 40 and/or the blocking element 30. So that the fixation rod 1 can be moved as freely as possible in the rod insertion device 10 in order to be able to achieve different angular positions, a slot 21 is provided in particular on the upper side of the receiving recess 22 which is as wide as the holding section of the fixation rod 1.

In FIGS. 4, 5 and 6, the proximal ends of the receiving body 20, of the blocking element 30 and of the clamping body 40 are represented enlarged. The receiving body 20 is shown in FIG. 6. The two guide grooves 24 are arranged at the sides of the receiving recess 22. The first area with the grooves in the axial direction is arranged in the entry area and can be easily produced by drilling or milling. The guide groove in the second area is much more difficult to produce since it preferably has a curvature. An effective method for providing this second area of the guide groove is a through hole 23, as is represented in FIGS. 2 and 6. At the proximal end of the receiving body there is a closable assembly opening 19. The assembly opening 19 is designed as a flap and makes it possible to insert and remove the parts (clamping body 40 and blocking element 30) located in the receiving body 20. This assembly opening can be closed with a flap with the result that the component parts cannot fall out of the receiving body.

The receiving body 20 is formed hollow in order to receive the blocking element 30 and the clamping body. On its inside, the receiving body 20 preferably has a protrusion which serves as positioning pin 27. This co-operates with a positioning surface 35 of the blocking element and fixes the blocking element in the circumferential direction in the receiving body. The positioning pin 27 is flattened at its end and rests loosely on the positioning surface 35, with the result that the blocking element 30 cannot twist in the receiving body 20.

The blocking element 30 is arranged inside the receiving body. It is hollow and preferably has a U- or O-shaped cross section. At the distal end, the blocking element 30 has a detent 32, which is formed here as a protrusion 32, which serves to block the guide bolt 3 located in the end position. Here, the protrusion is split into two so that the blocking element can reach around the fixation rod and pass over the bolts. The protrusion 32 can be formed inclined on the upper side at its end so that, when engaging in the force-fitting position described later, the guide bolts can push the blocking element 30 away or at least support the withdrawal by means of a slide lever 36. On its inside, the blocking element 30 preferably has a protrusion which serves as positioning pin 37. In FIG. 7 it can be seen that, in the embodiment shown, the pin 37 is located on the slide lever 36. This positioning pin 37 co-operates with a positioning area 45 of the clamping body 40 and fixes the clamping body 40 in the circumferential direction in the blocking element 30. The positioning pin 37 is flattened at its end and rests loosely on the positioning area 45, with the result that the clamping body 40 cannot twist in the blocking element 30.

At the proximal end, the blocking element is mounted spring-loaded. The spring 34 is mounted on the receiving body in the area of the grip and pre-stresses the blocking element 30 in the blocking position. This spring 34 can be arranged between the receiving body 20 and the blocking element 30, with the result that the whole blocking element can move in the receiving body 20. It can, however, also be formed as part of the blocking element 30. In this case, the blocking element is formed from component parts that are movable with respect to each other, with the result that the detent 32 is mounted movably on the blocking element and the spring is arranged between the movable part with the detent 32 and the part that is not moving relative to the receiving element. This solution is represented in FIG. 3.

In order to bring the blocking element 30 out of the blocking position (in which the fixation rod 1 is held in the force-fitting position) into an open position (in which the fixation rod 1 can be removed from the force-fitting position), the blocking element 30 has a slide lever 36, with which the blocking element 30 can be displaced inside the receiving element 20. The slide lever 36 is preferably attached at the rear end and goes through a recess on the receiving body provided there. The user can thus comfortably operate the slide lever 30 with one hand without the grip on the rod insertion device 10 having to be loosened or released.

The clamping body 40 is likewise preferably arranged inside the receiving body 20 and the blocking element 30. In particular, it is formed as an elongated and solid rod, which, at its proximal end, abuts at the contact point 26 against the operating lever 28 to strengthen the clamping force and, at its distal end, has a clamping geometry. This is provided in order to form a force fit with the proximal end 2 of the fixation rod 1. In principle, the force fit can be achieved for any desired angular adjustment of the fixation rod 1 merely by pressing the clamping body 40 onto the proximal end 2 of the fixation rod 1. For this purpose, the clamping body can have a tapering geometry, for example a tooth or a tip. The clamping force is thus concentrated on a small point and increased. If, in fact, a stepwise adjustment (therefore in pre-determined angular steps) is sufficient for the angular positioning, then the security of the force fit and specially the security against an unintentional twisting of the angular position can be increased. This can occur, for example, when the proximal end 2 of the fixation rod 1 has flat areas on its circumference, with the result that the clamping body can also be formed flat at the distal end. However, it is preferred for the end to be provided with a tooth geometry, which is provided in particular on a concave, inward-curving surface at the distal end. The tooth geometry is represented in FIG. 4, including the concave curvature of the end of the clamping body. The proximal end 2 of the fixation rod 1 then has a complementary surface with notches, in which the teeth can engage.

When using the rod insertion device 10 shown in the figures, the device is first of all assembled. For this purpose, the operating lever 28 is brought into an assembly position with the result that it is not in the way for the assembly. For the assembly position, the spring 29 is unhinged from the operating lever 28 and the lever 28 is folded right up away from the handle. Then, the blocking element 30 is inserted through the assembly opening 19 into the receiving body 20 and then the clamping body 40 is inserted into the blocking element 30. Depending on the embodiment of the blocking element 30, the spring can then be pushed over the clamping body 40. Then, the assembly opening 19 is closed with the flap 18 and the operating lever 28 is folded down into the operating position and engaged in the spring 29. Next, the fixation rod 1 is introduced into the receiving recess 22 in the first area of the guide groove 24. Then, the bolts 3 strike against the blocking protrusion 32, which is either pushed away via the inclined embodiment or which is pulled back by means of the slide lever 36. The guide bolts 3 are automatically pushed in the second direction further into the force-fitting position in the guide groove 24 and the blocking element 30 or the detent 32 engages again in the blocking position. The fixation rod 1 is now fixed in the force-fitting position but still twistable around the axis of the guide bolts 3. Then, the desired angular position of the fixation rod 1 is set, the operating lever 28 is pulled with the fingers, with the result that the clamping body 40 pushes against the proximal end 2 of the fixation rod 1 and is fixed in the angular position. The force fit of the end of the clamping body with the proximal end 2 of the fixation rod 1 is thus achieved in order to prevent twisting of the fixation rod. The operating lever 28 can then be fixed in its pulled-back position. After these steps, the fixation rod can be inserted. Repeated releasing/fixing of the fixation rod 1 allows a stepwise insertion of the fixation rod 1 into the pedicle screw(s). Depending on the embodiment of the clamping end 42 and the complementary embodiment of the proximal end 2 of the fixation rod 1, this is possible continuously or in pre-determined angular positions.

For the release of the fixation rod 1, the operating lever 28 is released again and pushed forward by the spring 29, and the force fit is thereby loosened, with the result that a slight movement is sufficient in order to release the engagement of the clamping body 40 at the proximal end 2 of the fixation rod 1. In order to disconnect the rod insertion device, the part of the blocking element 30 located in front of the spring 34 is pulled back on the slide lever 36.

The blocking protrusions 32 thereby release the bolts 3 of the fixation rod 1, these slide along the guide groove out of the force-fitting position into the first area of the guide groove and the rod insertion device 10 can be removed from the fixation rod 1. For cleaning, the assembly opening is then opened and the component parts are removed from the receiving element.

LIST OF REFERENCE NUMBERS

Fixation rod 1
Proximal end 2
Bolt 3
Conical tip 5
Bent section 7
Holding section 9
Rod insertion device 10
Handle 12
Flap 18
Assembly opening 19
Receiving body 20
Slot 21
Receiving recess 22
Through hole 23
Guide grooves 24
Contact point 26
Positioning pin 27
Operating lever 28
Spring 29
Blocking element 30
Blocking protrusion 32
Spring 34
Positioning area 35
Slide lever 36
Positioning pin 37
Clamping body 40
Clamping end 42
Positioning area 45

The invention claimed is:

1. A rod insertion device for insertion of a fixation rod into a pedicle screw, comprising:
    a receiving body comprising:
        a receiving recess at a distal end of the receiving body; and
        opposite guide grooves formed in the receiving body within the receiving recess, wherein the guide grooves are configured to receive guide bolts of the fixation rod; and
    a clamping body arranged in the receiving body that clamps the fixation rod in the receiving recess; wherein:
    in an entry area of the guide grooves, the guide grooves are formed in a first direction in the receiving body;
    in a force-fitting area of the guide grooves behind the entry area, the guide grooves are formed in a second direction different from the first direction in the receiving body; and
    the rod insertion device includes a blocking element having a detent, wherein the blocking element is movable between a release position and a blocking position, and wherein the guide bolts of the fixation rod are prevented from moving from the force-fitting area to the entry area when the clamping body engages the fixation rod and/or when the blocking element is in the blocking position.

2. The rod insertion device according to claim 1, wherein the blocking element is displaceable along an entry direction of the receiving recess.

3. The rod insertion device according to claim 2, wherein the blocking element includes at least one blocking protrusion at a distal end of the blocking element, and wherein the at least one blocking protrusion protrudes above the guide bolts when the blocking element is in the blocking position.

4. The rod insertion device according to claim 2, wherein the blocking element is spring-loaded in the receiving body and is pre-stressed when the blocking element is in the blocking position.

5. The rod insertion device according to claim 2, wherein the blocking element includes a slide control at a proximal end of the blocking element that displaces the blocking element.

6. The rod insertion device according to claim 1, wherein the clamping body includes a tapering geometry or a tooth geometry at a distal end of the clamping body.

7. The rod insertion device according to claim 1, wherein the receiving body, the clamping body and the blocking element are formed as longitudinally extending cylinder bodies.

8. The rod insertion device according to claim 7, wherein the clamping body is arranged in the blocking element and the blocking element is arranged in the receiving body.

9. The rod insertion device according to claim 1, wherein a handle is attached to the receiving body, the handle being formed as a pistol grip.

10. The rod insertion device according to claim 1, wherein the receiving body includes a closable assembly opening at a proximal end of the receiving body.

11. The rod insertion device according to claim 1, wherein the clamping body is pressed against a clamping area of the fixation rod by an operating lever.

12. The rod insertion device according to claim 1, wherein the first direction of the guide grooves in the entry area is along a longitudinal axis of the receiving body, and wherein the second direction of the guide grooves in the force-fitting area is downward relative to the first direction.

* * * * *